United States Patent [19]
Sembo

[11] Patent Number: 6,140,350
[45] Date of Patent: Oct. 31, 2000

[54] METHOD FOR CONTROLLING ECTOPARASITES

[75] Inventor: Satoshi Sembo, Takarazuka, Japan

[73] Assignee: Sumitomo Chemical Company, Limited, Osaka, Japan

[21] Appl. No.: 09/296,382

[22] Filed: Apr. 23, 1999

[30] Foreign Application Priority Data

Jun. 8, 1998 [JP] Japan .................................. 10-159260

[51] Int. Cl.$^7$ ...................... A61K 31/155; A61K 31/426; A61K 31/427; A61K 31/44

[52] U.S. Cl. .......................... 514/332; 514/342; 514/343; 514/352; 514/357; 514/365; 514/370; 514/426; 514/471; 514/472; 514/631; 514/634; 514/637

[58] Field of Search .................. 514/332, 342, 514/343, 352, 357, 365, 370, 426, 428, 408, 471, 472, 631, 634, 637

[56] References Cited

U.S. PATENT DOCUMENTS

| | | | |
|---|---|---|---|
| 4,742,060 | 5/1988 | Shiokawa et al. | 514/252 |
| 4,849,432 | 7/1989 | Shiokawa et al. | 514/341 |
| 5,034,404 | 7/1991 | Uneme et al. | 514/365 |
| 5,304,566 | 4/1994 | Ishimitsu et al. | 514/357 |
| 5,532,365 | 7/1996 | Kodaka et al. | 544/212 |
| 5,750,548 | 5/1998 | Friedel et al. | 514/357 |

FOREIGN PATENT DOCUMENTS

| | | |
|---|---|---|
| 2014495 | 5/1995 | Australia . |
| 0268915A2 | 6/1988 | European Pat. Off. . |
| 0428941 | 5/1991 | European Pat. Off. . |
| 0649845 | 4/1995 | European Pat. Off. . |
| 0682869A1 | 11/1995 | European Pat. Off. . |
| 4443888A1 | 6/1996 | Germany . |
| 19613334A1 | 10/1997 | Germany . |
| WO 9819532 | 5/1998 | WIPO . |

OTHER PUBLICATIONS

Jacobs D. et al., "Comparison of flea control strategies using imidacloprid or lufenuron on cats in a controlled simulated home environment," AJVR, vol. 58, No. 11, Nov. 1997, pp. 1260–1262.

Hopkins T., "Imidacloprid and resolution of signs of flea allergy dermatitis in dogs," Canine Practice, vol. 23, No. 2, Mar. 1998, pp. 18–20.

Arther R. et al., "Efficacy of imidacloprid for removal and control of fleas (Ctenocephalides felis) on dogs," AJVR, vol. 58, No. 8, Aug. 1997, pp. 848–850.

Franc M. et al., "Antifeeding effect of several insecticidal formulations against Ctenocephalides felis on cats", Parasite, vol. 5, No. 1, Mar. 1998, pp. 83–86.

Jacobs D. E. et al., "Duration of activity of imidacloprid, a novel adulticide for flea control, against Ctenocephalides felis on cats,"Vet Record, vol. 140, No. 10, Mar. 1997, pp. 259–260.

*Primary Examiner*—Phyllis G. Spivack
*Attorney, Agent, or Firm*—Birch, Stewart, Birch & Kolasch LLP

[57] ABSTRACT

A method for controlling ectoparasites systemically through host animal blood which comprises administering at least one neonocotinoid compound among those defined in the specification to the host animal.

5 Claims, No Drawings

METHOD FOR CONTROLLING ECTOPARASITES

FIELD OF THE INVENTION

The present invention relates to a method for systemic-controlling ectoparasites and an ectoparasite controlling agent.

BACKGROUND ART

It is known from ALL-B20144/95, regional application of a class of compounds to animals can prevent infection of ectoparasites.

However, such an application, which is for controlling ectoparasites non-systemically, was not always sufficiently quick-acting or long-lasting. For example, effective action is delayed except where applied directly. If not where applied directly, efficacy is lowered or unstable owing to bathing or washing of hair, body surface, etc.

SUMMARY OF THE INVENTION

The present invention provides an effective ectoparasite controlling method that is a method for controlling ectoparasites systemically through blood of a host animal which is characterized by applying at least one neonicotinoid compound (hereinafter, the present compound(s)) given in the following formula (1), (2) or (3):

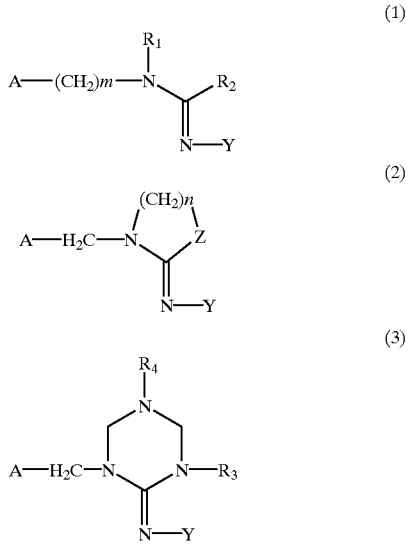

wherein, A represents 6-chloro-3-pyridyl, 2-chloro-5-thiazoly, tetrahydrofuran-2-yl, tetrahydrofuran-3-yl, 5-methyltetrahydrofuran-3-yl, 3-pyridyl, 6-bromo-3-pyridyl, 3-cyanophenyl, 2-methyl-5-thiazolyl, 2-phenyl-5-thiazolyl or 2-bromo-5-thiazolyl group; $R_1$ represents hydrogen atom, methyl, ethyl, formyl or acetyl group; $R_2$ represents methyl, amino, methylamino, N,N-dimethylamino, ethylamino, N,N-diethylamino, N-ethyl-N-methylamino, 1-pyrrolidinyl, (6-chloro-3-pyridyl)methylamino or N-methyl-N-(6-chloro-3-pyridyl)methylamino group; $R_3$ and $R_4$ represent methyl, ethyl, propyl, propenyl or propynyl group; Y represents cyano, nitro or trifluoroacetyl group; Z represents NH group or sulfur atom; m represents an integer of 0 or 1; and n represents an integer of 2 or 3, to the host animal, as well as an ectoparasite controlling agent for the use.

DETAILED DESCRIPTION OF THE INVENTION

The neonicotinoid compounds shown above have nitroimino, cyanoimino or trifluoroacetylimino groups and are known as active ingredients for insecticides. They are described, for example, in U.S. Pat. No. 5,532,365, U.S. Pat. No. 4,742,060, U.S. Pat. No. 4,849,432, U.S. Pat. No. 5,034,404, U.S. Pat. No. 5,304,566 and EP-428941A, and can be obtained according to the description.

Examples of the compounds given in the formula (1) include (E)-$N^1$-[(6-chloro-3-pyridyl)methyl]-$N^2$-cyano-$N^1$-methylacetamidine, 1-(6-chloro- 3-pyridyl)methyl-3-methyl-2-cyanoguanidine, 1-(6-chloro-3-pyridyl)methyl-1,3-dimethyl-2-cyanoguanidine, 1-(6-chloro-3-pyridyl)methyl-1-ethyl-3-methyl-2-cyanoguanidine, 1-(6-chloro-3-pyridyl)methyl-1,3-dimethyl-3-(6-chloro-3-pyridyl)methyl-2-cyanoguanidine, 1-(6-chloro-3-pyridyl)methyl-3-methyl-2-nitroguanidine, 1-(6-chloro-3-pyridyl)methyl-3,3-dimethyl-2-nitroguanidine, 1-(6-chloro-3-pyridyl)methyl-1-methyl-2-nitroguanidine, 1-(6-chloro-3-pyridyl)methyl-1,3-dimethyl-2-nitroguanidine, 1-(6-chloro-3-pyridyl)methyl-3-(6-chloro-3-pyridyl)methyl-2-nitroguanidine, 1-(6-chloro-3-pyridyl)methyl-1-ethyl-3-methyl-2-nitroguanidine, 1-(6-chloro-3-pyridyl)methyl-1,3,3-trimethyl-2-nitroguanidine, 1-(6-chloro-3-pyridyl)methyl-2-nitroguanidine, 1-(6-chloro-3-pyridyl)methyl-1-ethyl-2-nitroguanidine, 1-(3-pyridyl)methyl-3-methyl-2-nitroguanidine, 1-(6-bromo-3-pyridyl)methyl-3-methyl-2-nitroguanidine, 1-(2-chloro-5-thiazolyl)methyl-3-methyl-2-nitroguanidine, 1-(3-cyanophenyl)-3-methyl-2-nitroguanidine, 1-(4-chlorophenyl)methyl-3-methyl-2-nitroguanidine, 1-(6-chloro-3-pyridyl)methyl-3,3-dimethyl-1-formyl-2-nitroguanidine, 1-(6-chloro-3-pyridyl)methyl-3,3-dimethyl-1-acetyl-2-nitroguanidine, 1-(6-chloro-3-pyridyl)-3-methyl-2-cyanoguanidine, 1-(2-chloro-5-thiazolyl)methyl-3,3-dimethyl-2-nitroguanidine, 1-(2-chloro-5-thiazolyl)methyl-1-ethyl-3-methyl-2-nitroguanidine, 1-(2-chloro-5-thiazolyl) methyl-1-acetyl-3,3-dimethyl-2-nitroguanidine, 1-(2-chloro-5-thiazolyl)methyl-1,3-dimethyl-2-nitroguanidine, 1-(2-chloro-5-thiazolyl)methyl 1-methyl-2-nitroguanidine, 1-(5-thiazolyl)methyl-3-methyl-2-nitroguanidine, 1-(2-methyl-5-thiazolyl)methyl-3,3-dimethyl-2-nitroguanidine, 1-(2-methyl-5-thiazolyl)methyl-3-methyl-2-nitroguanidine, 1-(2-phenyl-5-thiazolyl)methyl-3-methyl-2-nitroguanidine, 1-(2-chloro-5-thiazolyl)methyl-3,3-diethyl-2-nitroguanidine, 1-(2-chloro-5-thiazolyl)methyl-3-methyl-3-ethyl-2-nitroguanidine, 1-(2-chloro- 5-thiazolyl)methyl-3-(1-pyrrolidinyl)-2-nitroguanidine, 1-(2-chloro-5-thiazolyl)methyl-1,3,3-trimethyl-2-nitroguanidine, 1-(2-bromo-5-thiazolyl)methyl-3-methyl-2-nitroguanidine, 1-(2-bromo-5-thiazolyl)methyl-3,3-dimethyl-2-nitroguanidine, 1-(2-chloro-5-thiazolyl)methyl-3-methyl-2-cyanoguanidine, 1-(tetrahydrofuran-3-yl)methyl-3-methyl-2-nitroguanidine and 1-(tetrahydrofuran-2-yl)methyl-3-methyl-2-nitroguanidine.

Examples of the compounds given in the formula (2) include 1-(2-chloro-5-pyridylmethyl)-2-cyanoiminothiazoline and 1-[(6-chloro-3-pyridyl)methyl]-N-nitrotetrahydropyrimidine-2-imine.

Examples of the compounds given in the formula (3) include 3,5-dimethyl-1-[(6-chloro-3-pyridyl)methyl]-N-nitrohexahydro-1,3,5-triazine-2-imine, 3,5-dimethyl-1-[(2-chloro-5-thiazolyl)methyl]-2-nitroiminohexahydro-1,3,5-triazine, 3-ethyl-5-methyl-1-[(6-chloro-3-pyridyl)methyl]-N-nitrohexahydro-1,3,5-triazine-2-imine, 3-n-propyl-5-methyl-1-[(6-chloro-3-pyridyl)methyl]-N-nitrohexahydro-1,3,5-triazine-2-imine, 3-n-propyl-5-methyl-1-[(2-chloro-5-thiazolyl)methyl]-N-nitrohexahydro-1,3,5-triazine-2-imine, 3-(2-propenyl)-5-methyl-1-[(6-chloro-3-pyridyl)methyl]-N-nitrohexahydro-1,3,5-triazine-2-imine and 3-(2-propynyl)-

5-methyl-1-[(6-chloro-3-pyridyl)methyl]-N-nitrohexahydro-1,3,5-triazine-2-imine.

In the present invention, the word "systemic control" means that the applied agent moves into blood of a host animal, the concentration of the agent in the blood is kept at a certain level and ectoparasites are controlled all over the body through the blood of the host animal.

In the controlling method of the present invention, the present compound is applied to a host animal usually at a dosage of 0.01 to 1000 mg, preferably 0.1 to 100 mg per 1 kg of the animal weight.

Examples of administration methods for the present compound to move into host animal blood, are oral or non-oral administrations, implantation and so on.

Examples of the oral administration include a method for applying feed mixed with the present compound to host animal and a method for applying a suitable formulation to animal wherein the formulation is easy to swallow for the animal such as biscuit, wafer, tablet, liquid and capsule.

Suitable carriers for these formulations include sugars such as lactose, sucrose, mannitol, sorbitol, cellulose and cellulose derivatives; excipients such as calcium phosphate; binders such as starch paste (utilized with corn, wheat, rice or potato starch), gelatin, tragacanth, methylcellulose, agar, alginic acid and alginic salts; lubricant such as silica, talc, stearic acid and stearic salt; and formulation cores that are sugar solution containing gum arabic, talc, polyvinylpyrrolidone, titanium dioxide or the like. The formulations may optionally comprise coloring agent or seasoning.

Further examples of the formulations for oral administration include dry capsules encapsulated a mixture of the present compound, excipients such as lactose, binder such as starch, lubricant such as talc and magnesium stearate and stabilizer in dry capsules of gelatin, and sealed soft capsules encapsulated the present compound dissolved or suspended in a suitable liquid such as fatty oil and paraffin oil or a mixture of the solution or suspension with a stabilizer in soft capsules comprising gelatin and plasticizer (e.g. glycerin, sorbitol).

Non-oral administration is usually an injection administration. Examples of the non-oral administration include an endermism with a percutaneous absorptive formulation, a hypodermoclysis utilized with a hypodermic injection formulation, an intramuscular administration utilized with a intramuscular injection formulation and an intravenous administration utilized with an intravenous injection formulation. For these administration, a liquid formulation such as solution, suspension and emulsion of the present compound is utilized. The liquid formulation includes aqueous solvents such as water, physiological saline and Ringer's solution; or lipophilic solvents such as fatty oil, sesame oil, corn oil and synthetic fatty acid ester. The aqueous solution containing the aqueous solvent is usually prepared from a water-soluble salt of the present compound.

A method for implanting a formulation of resin spread or molded the present compound to a host animal may be utilized.

In the controlling method of the present invention, the other insecticidal ingredient may be utilized together with the present compound.

Examples of the other insecticidal ingredients include insect growth regulating substances such as methoprene, hydroprene, lufenuron, chlorfluazuron, flufenoxuron, hexaflumuron, diflubenzuron, 1-(2,6-difluorobenzoyl)-3-[2-fluoro-4-(1, 1, 2, 3, 3, 3-hexafluoropropoxy)phenyl]urea, cyromazine and tebfenozide; insecticidal substances such as N-phenylpyrazoles; and endoparasite-controlling substances such as milbemycin, abamectin and avermectin.

Examples of the ectoparasites controlled by the present invention include Diptera such as *Musca hervei, Musca bezzii, Haematobia irritans, Simulium iwatens, Culicoides oxystoma, Tabanus chrysurus, Culex pipiens* (common mosquito) and *Aedes albopictus*; Anoplura (lice) such as *Haematopinus eurysternus* and *Damalinia ovis*; and Siphonaptera (fleas) such as *Ctenocephalides felis* (cat flea), *Ctenocephalides canis* (dog flea) and *Xenopsylla cheopis*.

The host animals include farm animals and pets. Examples of the farm animals include cattle and sheep, and examples of the pets include Rodentia such as mice, rats, hamsters and squirrels; Lagomorpha such as rabbits; Carnivora such as dogs, cats and ferrets; and Aves (birds) such as ducks, chickens, doves, and the like.

EXAMPLES

Below, the present invention is explained with the examples in detail.

Formulation example 1

Thirty miligrams (30 mg) of 1-(tetrahydrofuran-3-yl)methyl-3-methyl-2-nitroguanidine, 70 g of dextrin, 20 g of potato starch, 6 g of powder food for animals (CE-2 produced from Oriental Kobo Company), 2 g of sesame oil and 2 g of water are mixed and kneaded. The obtained powder (1 g) is molded and pressed at about 8 tons to afford a tablet.

Test example

A designated amount of 1-(tetrahydrofuran-3-yl)methyl-3-methyl-2-nitroguanidine (referred as Compound A in table 1) suspended in a 0.05% aqueous solution of methylcellulose was orally administered to a mouse (weight: about 30 g) with a sonde at a dosage of 10 mL per 1 kg of weight. The mouse was hold and fixed with wire net and put in a glass container of 900 mL volume. Twenty adult cat fleas (unbloodsucked) were deposited. The mortality of adult fleas was examined 24 hours after administration. Each test was repeated thrice. The result is given in table 1.

As a comparative test, a corn oil dilution of cyphenothrin (referred as Comparative compound 1 in table 1) was applied to a mouse at a dosage of 25 mg/kg, tested in the same manner as above and the mortality of adult fleas was examined 24 hours later. The result is given in table 1.

TABLE 1

|  | Dosage (mg/kg) | Mortality of cat flea (%) |
| --- | --- | --- |
| Compound A | 10.0 | 65.0 |
| Comparative compound 1 | 25.0 | 0.0 |

Reference example

A designated amount of an acetone solution of 1-(tetrahydrofuran-3-yl)methyl-3-methyl-2-nitroguanidine (referred as Compound A in table 2) was applied onto a filter paper. Twenty adult cat fleas were forced to contact with the filter paper and the mortality was examined 24 hours later. Each test was repeated thrice. The result is given in table 2. Further, cat fleas were forced to contact with the filter paper treated with cyphenothrin (referred as Comparative compound 1 in table 2) as a reference and the mortality was examined 24 hours later. Each test was repeated thrice. The result is given in table 2.

TABLE 2

| | Dosage (mg/kg) | Mortality of cat flea (%) |
|---|---|---|
| Compound A | 160 | 24 |
| Comparative compound 1 | 100 | 88 |

As shown in the test example and reference example, Compound A is effective for systemic-controlling of fleas though Compound A is not so suitable for controlling fleas at direct contact.

What is claimed is:

1. A method for controlling ectoparasites through blood of a host animal which comprises applying at least one neonicotinoid compound given in the following formula (1):

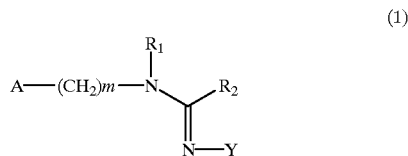

wherein, A represents 6-chloro-3-pyridyl, 2-chloro-5-thiazolyl, tetrahydrofuran-2-yl, tetrahydrofuran-3-yl, 5-methyltetrahydrofuran-3-yl, 3-pyridyl, 6-bromo-3-pyridyl, 3-cyanophenyl, 2-methyl-5-thiazolyl, 2-phenyl-5-thiazolyl or 2-bromo-5-thiazolyl group; $R_1$ represents hydrogen atom, methyl, ethyl, formyl or acetyl group; $R_2$ represents methyl, amino, methylamino, N,N-dimethylamino, ethylamino, N,N-diethylamino, N-ethyl-N-methylamino, 1-pyrrolidinyl, (6-chloro-3-pyridyl)methylamino or N-methyl-N-(6-chloro-3-pyridyl)methylamino group; Y represents cyano, nitro or trifluoroacetyl group; and m represents an integer of 0 or 1; to the host animal, wherein the method is an oral administration, injection administration or implantation.

2. A method according to claim 1, wherein the dosage of the neonicotinoid compound is 0.1 to 100 mg per 1 kg of a host animal weight.

3. A method according to claim 2, wherein the neonicotinoid compound is 1-(tetrahydrofuran-3-yl)methyl-3-methyl-2-nitroguanidine.

4. A method according to claim 1, wherein the neonicotinoid compound is 1-(tetrahydrofuran-3-yl)methyl-3-methyl-2-nitroguanidine.

5. A method for controlling ectoparasites through the blood of a host animal which comprises administering at least one neonicotinoid selected from the group consisting of (E)-$N^1$-[(6-chloro-3-pyridyl)methyl]-$N^2$-cyano-$N^1$-methylacetamidine, 1-(6-chloro-3-pyridyl)methyl-3-methyl-2-cyanoguanidine, 1-(6-chloro-3-pyridyl)methyl-1,3-dimethyl-2-cyanoguanidine, 1-(6-chloro-3-pyridyl)methyl-1-ethyl-3-methyl-2-cyanoguanide, 1-(6-chloro-3-pyridyl)methyl-1,3-dimethyl-3-(6-chloro-3-pyridyl)methyl-2-cyanoguanidine, 1-(6-chloro-3-pyridyl)methyl-3-methyl-2-nitroguanidine, 1-(6-chloro-3-pyridyl)methyl-3,3-dimethyl-2-nitroguanidine, 1-(6-chloro-3-pyridyl)methyl-1-methyl-2-nitroguanidine, 1-(6-chloro-3-pyridyl)methyl-1,3-dimethyl-2-nitroguanidine, 1-(6-chloro-3-pyridyl)methyl-3-ethyl-2-nitroguanidine, 1-(6-chloro-3-pyridyl)methyl-3-(6-chloro-3-pyridyl)methyl-2-nitroguanidine, 1-(6-chloro-3-pyridyl)methyl-1-ethyl-3-methyl-2-nitrogauanidine, 1-(6-chloro-3-pyridyl)methyl-1,3,3-trimethyl-2-nitroguanidine, 1-(6-chloro-3-pyridyl)methyl-2-nitroguanidine, 1-(6-chloro-3-pyridyl)methyl-1-ethyl-2-nitroguanidine, 1-(3-pyridyl)methyl-3-methyl-2-nitroguanidine, 1-(6-bromo-3-pyridyl)methyl-3-methyl-2-nitroguanidine, 1-(2-chloro-5-thiazolyl)methyl-3-methyl-2-nitroguanidine, 1-(3-cyanophenyl)-3-methyl-2-nitroguanidine, 1-(4-chlorophenyl)methyl-3-methyl-2-nitroguanidine, 1-(6-chloro-3-pyridyl)methyl-3,3-dimethyl-1-formyl-2-nitroguanidine, 1-(6-chloro-3-pyridyl)methyl-3,3-dimethyl-1-acetyl-2-nitroguanidine, 1-(6-chloro-3-pyridyl)-3-methyl-2-cyanoguanidine, 1-(2-chloro-5-thiazolyl)methyl-3,3-dimethyl-2-nitroguanidine, 1-(2-chloro-5-thiazolyl)methyl-1-ethyl-3-methyl-2-nitroguanidine, 1-(2-chloro-5-thiazolyl)methyl-1-acetyl-3,3-dimethyl-2-nitroguanidine, 1-(2-chloro-5-thiazolyl)methyl-1,3-dimethyl-2-nitroguanidine, 1-(2-chloro-5-thiazolyl)methyl-1-methyl-2-nitroguanidine, 1-(5-thiazolyl)methyl-3-methyl-2-nitroguanidine, 1-(2-methyl-5-thiazolyl)methyl-3,3-dimethyl-2-nitroguanidine, 1-(2-methyl-5-thiazolyl)methyl-3-methyl-2-nitroguanidine, 1-(2-phenyl-5-thiazolyl)methyl-3-methyl-2-nitroguanidine, 1-(2-chloro-5-thiazolyl)methyl-3,3-diethyl-2-nitroguanidine, 1-(2-chloro-5-thiazolyl)methyl-3-methyl-3-ethyl-2-nitroguanidine, 1-(2-chloro-5-thiazolyl)methyl-3-(1-pyrrolidinyl)-2-nitroguanidine, 1-(2-chloro-5-thiazolyl)methyl-1,3,3-trimethyl-2-nitroguanidine, 1-(2-bromo-5-thiazolyl)methyl-3-methyl-2-nitroguanidine, 1-(2-bromo-5-thiazolyl)methyl-3,3-dimethyl-2-nitroguanidine, 1-(2-chloro-5-thiazolyl)methyl-3-methyl-2-cyanoguanidine, 1-(tetrahydrofuran-3-yl)methyl-3-methyl-2-nitroguanidine and 1-(tetrahydrofuran-2-yl)methyl-3-methyl-2-nitroguanidine.

* * * * *